(12) United States Patent
DellaRovere et al.

(10) Patent No.: US 9,618,483 B2
(45) Date of Patent: Apr. 11, 2017

(54) FITTING ASSEMBLIES

(75) Inventors: Dennis DellaRovere, Mendon, MA (US); James P. Murphy, Franklin, MA (US)

(73) Assignee: Waters Technologies Corporation, Milford, MA (US)

( * ) Notice: Subject to any disclaimer, the term of this patent is extended or adjusted under 35 U.S.C. 154(b) by 479 days.

(21) Appl. No.: 14/113,391

(22) PCT Filed: Apr. 20, 2012

(86) PCT No.: PCT/US2012/034342
§ 371 (c)(1),
(2), (4) Date: Nov. 13, 2013

(87) PCT Pub. No.: WO2012/148793
PCT Pub. Date: Nov. 1, 2012

(65) Prior Publication Data
US 2014/0053639 A1  Feb. 27, 2014

Related U.S. Application Data

(60) Provisional application No. 61/478,761, filed on Apr. 25, 2011.

(51) Int. Cl.
*F16L 19/06* (2006.01)
*G01N 30/02* (2006.01)
(Continued)

(52) U.S. Cl.
CPC .............. *G01N 30/02* (2013.01); *F16L 17/02* (2013.01); *F16L 19/065* (2013.01);
(Continued)

(58) Field of Classification Search
CPC ......... B01D 15/08; F16L 19/06; F16L 19/065
(Continued)

(56) References Cited

U.S. PATENT DOCUMENTS 2,499,104 A * 2/1950 Lovell .................. F16L 19/005
 285/349
4,283,280 A   8/1981 Brownlee
(Continued)

FOREIGN PATENT DOCUMENTS

GB   2 306 593 A   5/1997
JP   07-253422 A   10/1995
(Continued)

OTHER PUBLICATIONS

PCT International Search Report for PCT/US12/34342, date of mailing Jul. 31, 20912, 3 pages.
(Continued)

*Primary Examiner* — Beth Stephan
(74) *Attorney, Agent, or Firm* — Waters Technologies Corporation

(57) ABSTRACT

A fitting assembly includes a first fitting that is configured to receive a first fluid tube and a second fitting that is configured to receive a second fluid tube. The first fitting defines a first groove. The second fitting includes a spring that is configured to engage the first groove to connect the first and second fittings such that the first and second fluid tubes are placed in fluid communication and a fluid tight seal is established between the first and second sealing fittings.

24 Claims, 8 Drawing Sheets

(51) Int. Cl.
*G01N 30/60* (2006.01)
*F16L 19/065* (2006.01)
*F16L 37/084* (2006.01)
*F16L 17/02* (2006.01)

(52) U.S. Cl.
CPC ........ *F16L 37/084* (2013.01); *G01N 30/6026* (2013.01); *G01N 30/6034* (2013.01)

(58) Field of Classification Search
USPC ........................................ 285/342, 343, 353
See application file for complete search history.

(56) References Cited

U.S. PATENT DOCUMENTS

| | | | |
|---|---|---|---|
| 4,313,828 A | 2/1982 | Brownlee | |
| 4,690,437 A * | 9/1987 | Anderson, Jr. | G01N 30/6026 285/339 |
| 4,876,005 A | 10/1989 | America | |
| 5,163,722 A * | 11/1992 | Worden | F16L 37/242 285/101 |
| 5,234,235 A * | 8/1993 | Worden | F16L 29/04 285/334.4 |
| 5,288,113 A * | 2/1994 | Silvis | G01N 30/6026 285/334.4 |
| 5,298,225 A | 3/1994 | Higdon | |
| 5,411,348 A * | 5/1995 | Balsells | F16B 9/02 174/372 |
| 5,525,303 A | 6/1996 | Ford et al. | |
| 5,540,464 A | 7/1996 | Picha | |
| 5,545,842 A * | 8/1996 | Balsells | F16B 9/02 174/351 |
| 5,582,723 A * | 12/1996 | Boone | G01N 30/6091 210/198.2 |
| 5,651,885 A * | 7/1997 | Schick | B01D 15/22 210/198.2 |
| 5,718,459 A | 2/1998 | Davie et al. | |
| 5,727,821 A * | 3/1998 | Miller | F16L 37/088 285/308 |
| 5,730,943 A | 3/1998 | Ford et al. | |
| 5,775,738 A | 7/1998 | Bartholomew | |
| 5,911,954 A | 6/1999 | Ford et al. | |
| 6,056,331 A * | 5/2000 | Benett | F16L 19/02 285/334.4 |
| 6,095,572 A | 8/2000 | Ford et al. | |
| 6,361,687 B1 | 3/2002 | Ford et al. | |
| 6,450,545 B1 * | 9/2002 | LeMay | F16L 37/088 285/316 |
| 6,749,358 B2 * | 6/2004 | Balsells | H01R 13/187 403/315 |
| 6,835,084 B2 | 12/2004 | Poon et al. | |
| 6,857,665 B2 * | 2/2005 | Vyse | F16L 19/005 285/276 |
| 7,156,424 B2 * | 1/2007 | McCord | F16L 19/005 285/319 |
| 7,210,398 B2 * | 5/2007 | Balsells | F16J 1/008 277/437 |
| 7,229,551 B2 * | 6/2007 | Murata | G01N 30/34 210/198.2 |
| 7,274,964 B2 * | 9/2007 | Balsells | A61N 1/3752 267/166 |
| 7,641,242 B2 * | 1/2010 | Van Pelt | B01L 3/565 285/353 |
| 8,128,131 B2 * | 3/2012 | Barnett | F16L 7/02 285/332 |
| 2005/0077222 A1 * | 4/2005 | Dawes | G01N 30/6026 210/198.2 |
| 2006/0113794 A1 * | 6/2006 | Plant | G01N 30/6004 285/339 |
| 2007/0164562 A1 * | 7/2007 | Valaskovic | G02B 6/3809 285/245 |
| 2010/0224546 A1 * | 9/2010 | Ellis | G01N 30/6039 210/232 |
| 2011/0198842 A1 * | 8/2011 | Murphy | B01L 3/565 285/330 |
| 2012/0228872 A1 * | 9/2012 | Gamache | F16L 19/065 285/331 |

FOREIGN PATENT DOCUMENTS

| | | |
|---|---|---|
| JP | 08-277984 A | 10/1996 |
| JP | 09-105491 A | 4/1997 |
| JP | 2002-509231 A | 3/2002 |
| WO | 93/13415 A1 | 7/1993 |

OTHER PUBLICATIONS

PCT International Written Opinion Report for PCT/US/2134342, Date of mailing Jul. 31, 20912, 5 pages.
[No Author Listed] Optimize Technologies Inc. website/Opti-Lok™ technology; accessed Jul. 27, 2016.
Extended European Search Report for Application No. 12776363.9, issued Aug. 10, 2014 (6 pages).
Japanese Office Action for Application No. 2014-508439, issued Mar. 8, 2016 (10 pages).

* cited by examiner

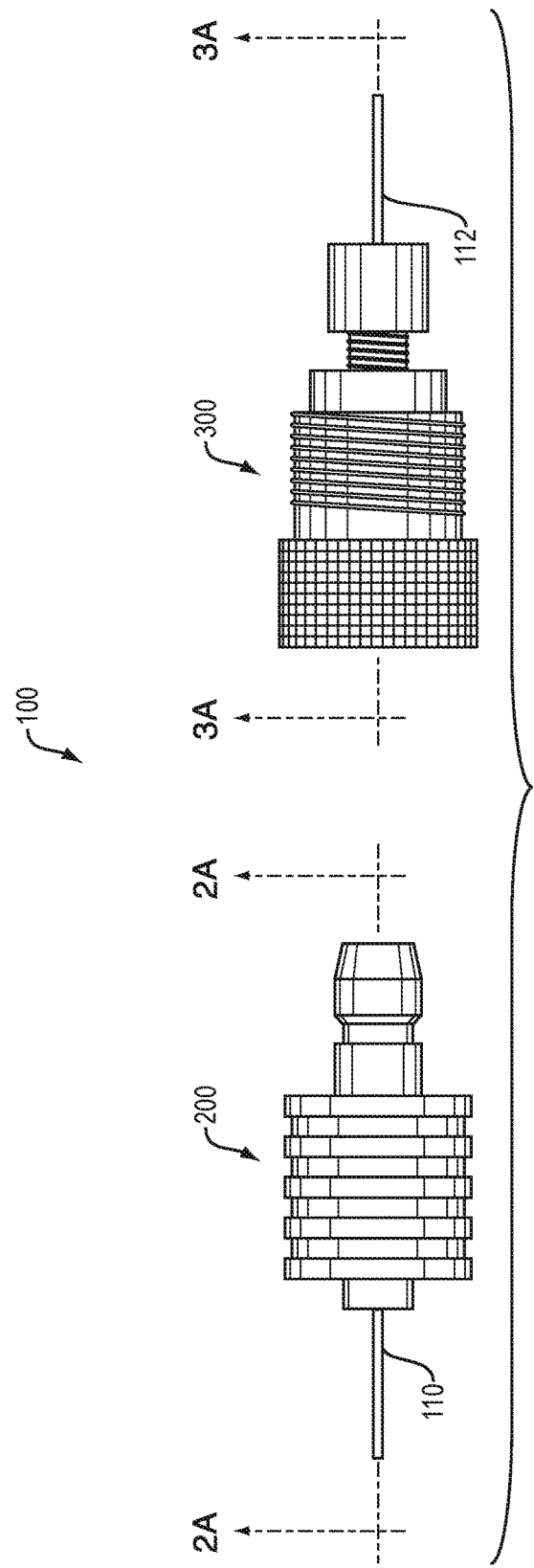

FITTING ASSEMBLIES

CROSS REFERENCE TO RELATED APPLICATIONS

This application is the National Stage of International Application No. PCT/US2012/034342, filed on Apr. 20, 2012, which claims priority to benefit of U.S. Provisional Patent Application Ser. No. 61/478,761, filed Apr. 25, 2011. The entire contents and teachings of these applications of are hereby expressly incorporated herein by reference in their entirety.

TECHNICAL FIELD

This invention generally relates to fitting assemblies, and, more particularly, to fitting assemblies for fluidic systems, such as chromatography systems.

BACKGROUND

Many fluidic systems, such as chromatography systems, include fluidic tubing for providing fluid communication between system components. For example, chromatography systems (e.g., liquid chromatography systems) typically include components, such as pumps, valves, columns, and detectors, that are connected together through fluidic (e.g., metallic or polymeric) tubing. These components and the fluidic tubing are often connected using threaded fittings or bayonet fittings. Connection and disconnection of these fittings (e.g., during assembly, repair, and/or replacement) can require application of torque, e.g., by hand alone or with the use of tools, to establish a fluid tight connection. This can be time consuming, cumbersome (e.g., in cases in which multiple turns are required), and may lead to leaks and/or failure if the fittings are not threaded together properly and/or if adequate torque is not applied when the connection is made.

SUMMARY

The invention arises, in part, from the realization that a fitting connection for connecting fluidic tubing can be configured to provide a fluid tight connection that does not require the application of torque, such as is required in conventional fittings having threaded or bayonet connections. Such configurations can allow for a simplified fluidic connection that may require less time and effort to establish a fluidic connection, and may also make disconnection easier and quicker. For example, the invention may be particularly well suited to provide improved fluidic connections in a chromatography system, such as at a liquid chromatography-mass spectroscopy (LC-MS) interface.

In one aspect, the invention provides a fitting assembly that includes a first fitting that is configured to receive a first fluid tube and a second fitting that is configured to receive a second fluid tube. The first fitting defines a first groove. The second fitting includes a spring that is configured to engage the first groove to connect the first and second fittings such that the first and second fluid tubes are placed in fluid communication and a fluid tight seal is established between the first and second sealing fittings.

Implementations may include one or more of the following features.

In some implementations, the first fitting defines a recess (e.g., an annular recess) which terminates at a first sealing face, and the second fitting defines a protrusion (e.g., a frustoconical protrusion) which terminates at a second sealing face. The protrusion is sized to fit within the recess such that the first sealing face abuts against the second sealing face to form the fluid tight seal when the first and second fittings are connected.

In certain implementations, the first fitting defines a recess (e.g., an annular recess), and the second fitting defines a protrusion (e.g., a frustoconical protrusion). The recess and the protrusion can have an interference fit to form the fluid tight seal when the first and second fittings are connected.

In some cases, the second fitting includes a fitting body that defines a cylindrical bore, and the first fitting includes a tubular body that is configured to be at least partially inserted into the cylindrical bore to establish a connection between the first and second fittings.

In certain cases, the spring is disposed within the cylindrical bore. For example, the fitting body can define a second groove within the cylindrical bore, and the spring can be disposed within the second groove.

In some examples, the spring is a garter spring.

In certain examples, the fluid tight seal is fluid tight at least up to 2500 pounds per square inch (PSI).

In some implementations, the first fitting includes a tubular body that defines a central passage for receiving the first fluid tube.

In certain implementations, the tubular body includes a beveled annular surface within the central passage, and the first fitting includes a ferrule that is configured to engage the beveled annular surface and to receive and retain the first fluid tube.

In some cases, the tubular body includes an internally threaded region within the central passage, and the first fitting includes a compression screw that is configured to threadingly engage the internally threaded region to retain the ferrule within the central passage.

In certain cases, the compression screw includes an internal passage that is configured to receive the first fluid tube.

In some examples, the tubular body includes a first fitting end that has knurled outer surface, and a second fitting end that includes a tapered tip. The second fitting end can define the first groove.

In certain examples, the first groove extends annularly about the tubular body.

In some implementations, the second fitting includes an insert that defines a central passage for receiving the second fluid tube, and a fitting body that defines a bore that is configured to receive the insert.

In certain implementations, the bore includes a latching portion for receiving the first fitting, and an insert portion for receiving the insert.

In some cases, the fitting body defines a second groove within the latching portion of the bore, and the spring is disposed within the second groove.

In some examples, the insert includes a beveled annular surface within the central passage, and the second fitting includes a ferrule that is configured to engage the beveled annular surface and to receive and retain the second fluid tube.

In certain examples, the insert includes an internally threaded region within the central passage, and the second fitting includes a compression screw that is configured to threadingly engage the internally threaded region to retain the ferrule within the central passage.

In some implementations, the compression screw includes an internal passage that is configured to receive the second fluid tube.

In certain implementations, the fitting assembly is incorporated in a chromatography system (e.g., a liquid chromatography (LC) system).

In some cases, the chromatography system includes a chromatography column, and a detector for measuring physical or chemical properties of fluid received from the chromatography column. The fitting assembly can be disposed between the chromatography column and the detector for establishing a fluidic connection therebetween.

In certain cases, the chromatography system includes a chromatography column, and a pump for conveying fluid toward the chromatography column. The fitting assembly can be disposed between the chromatography column and the pump for establishing a fluidic connection therebetween.

Other aspects, features, and advantages are in the description, drawings, and claims.

BRIEF DESCRIPTION OF THE DRAWINGS

FIG. 1B is a side view of the quick connect fitting assembly of FIG. 1 with the male fitting and the bulkhead fitting in a disconnected state.

Like reference numbers indicate like elements.

DETAILED DESCRIPTION

Figure 1A:
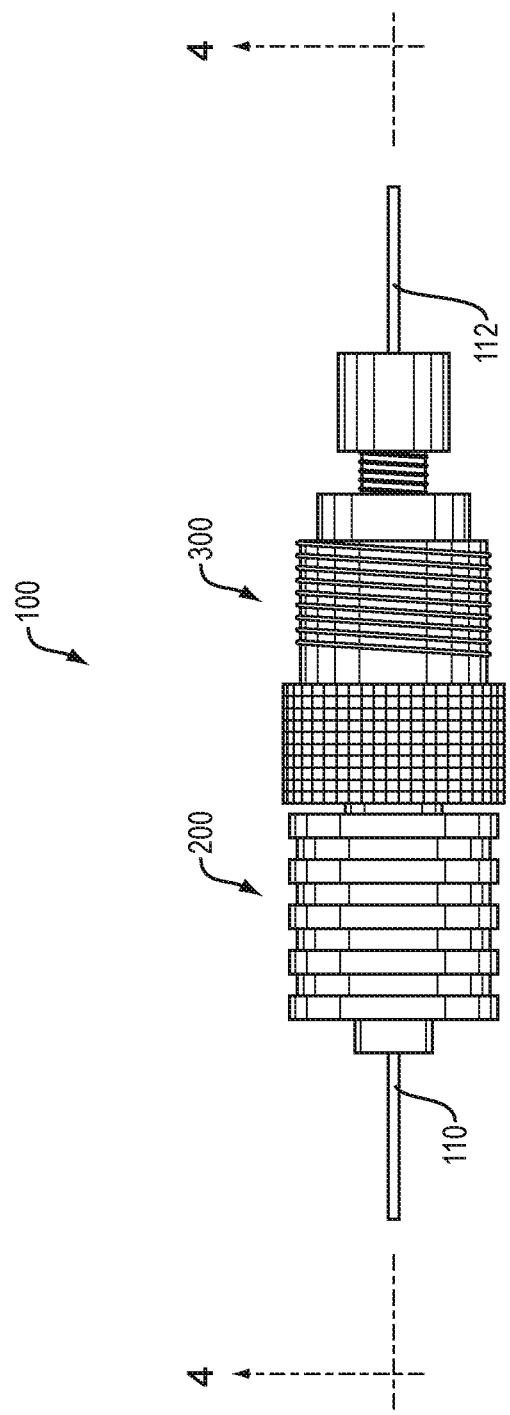
FIG. 1A is a side view of a quick connect fitting assembly having a male fitting and a bulkhead fitting in a connected state.

FIGS. 1A & 1B illustrate a quick connect fitting assembly 100 for connecting a first fluid tube 110 and a second fluid tube 112. The quick connect fitting assembly 100 includes a male fitting 200 and a bulkhead fitting 300 which latch together to provide a fluid-tight connection. Unlike convention threaded connections and bayonet (e.g., quarter turn) connections, the quick connect fitting assembly 100 can allow a fluid tight connection to be made without the application of torque. Consequently, a simplified connection scheme can be provided in which a fluid tight connection can be accomplished by merely inserting the male fitting 200 into the bulkhead fitting 300 without relying on torque to establish and maintain a fluid connection or having to rotate the male and bulkhead fittings 200, 300 relative to each other.

Figure 2A:
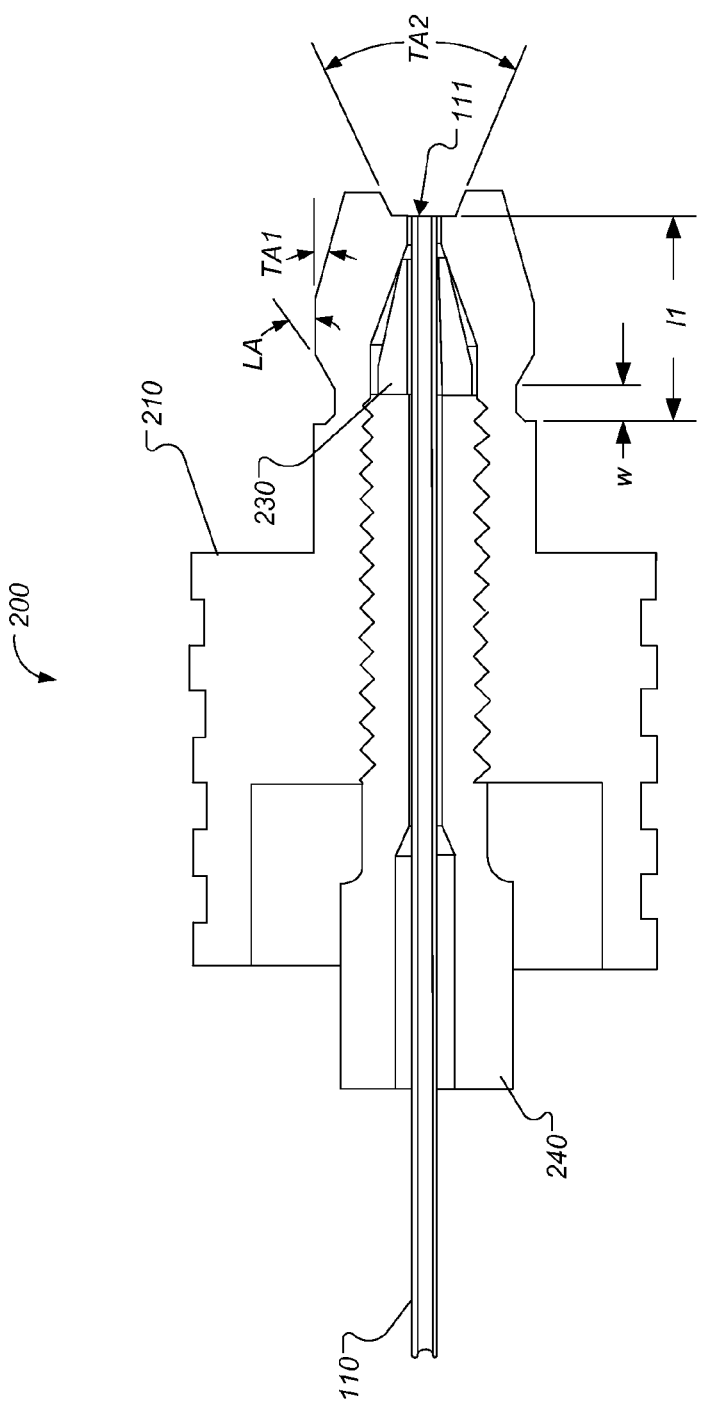
FIG. 2A is a cross-sectional view of the male fitting of FIG. 1B, taken along line 2A-2A.
Figure 2B:
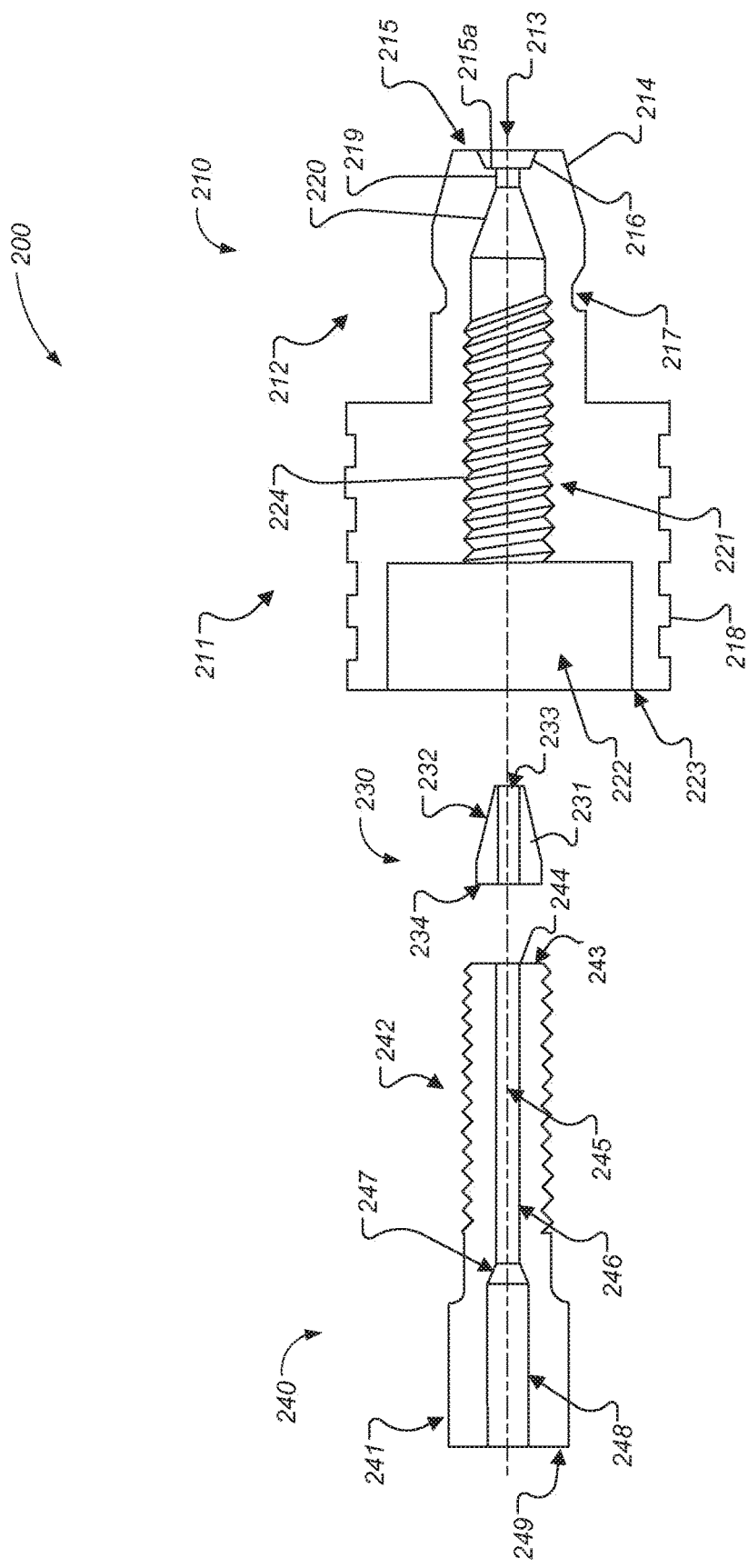
FIG. 2B is an exploded view of the male fitting of FIG. 2A.

Referring to FIGS. 2A & 2B, the male fitting 200 includes a tubular body 210, a first ferrule 230, and a first compression screw 240. As shown in FIG. 2B, the tubular body 210 has a proximal fitting end 211 and a distal fitting end 212. A central passage 213 extends from the proximal fitting end 211 to the distal fitting end 212 of the tubular body 210.

The tubular body 210 can have a single piece construction, being molded, machined or otherwise formed from a suitable material such as thermoplastic resin, or a metal. The tubular body 210 has an overall tubular configuration, with a diameter of the proximal fitting end 211 being greater than a diameter of the distal fitting end 212. For example, in some cases, the proximal fitting end 211 has a diameter of 0.48 inches to 0.52 inches, e.g., 0.50 inches, and the distal fitting end 212 has a diameter 0.235 inches to 0.239 inches (e.g., 0.237 inches).

The distal fitting end 212 has a tapered distal tip 214 that terminates at a distal surface 215. The tapered distal tip 214 has a taper angle TA1 (FIG. 2A) of 13 degrees to 17 degrees (e.g., 15 degrees). The distal surface 215 defines a distal sealing face 215a and a beveled annular recess 216. At its smallest point, i.e., at a junction with the distal sealing face 215a, the beveled annular recess 216 has a diameter of 0.067 inches to 0.077 inches (e.g., 0.072 inches), a depth of 0.013 inches to 0.017 inches (e.g., 0.015 inches), and a taper angle TA2 (FIG. 2A) of 49.5 degrees to 50.5 degrees (e.g., 50 degrees). The distal fitting end 212 also includes an annular groove 217 that is formed between the tapered distal tip 214 and the proximal fitting end 211. The annular groove 217 has a groove diameter of 0.194 inches to 0.198 inches, e.g., 0.196 inches, a width w (FIG. 2A) of 0.037 inches to 0.043 inches, e.g., 0.040 inches, and includes a tapered latching edge 217a, which extends at a latching angle LA (FIG. 2A) of 29.5 degrees to 30.5 degrees, e.g., 30.0 degrees. The annular groove 217 is spaced a distance D2 of 0.228 inches to 0.032 inches (e.g., 0.030 inches) away from the distal sealing face 215a, as measured from a proximal edge of the annular groove 217 to the distal sealing face 215a.

In some implementations, the tubular body 210 is formed from polyether-ether-ketone, such as PEEK™ polymer (available from Victrex PLC, Lancashire, United Kingdom), and is finished along the distal surface 215, e.g., at least at the distal sealing face 215a, to have a surface roughness Ra of 8 microinches to 32 micro inches (e.g., 16 microinches).

The proximal fitting end 211 has a knurled external surface 218. The central passage 213 has small diameter distal portion 219 that flares outwardly to form a beveled annular surface 220. The beveled annular surface 220 thus defines a frustoconical recess formed centrally within the tapered distal tip 214. The central passage 213 also includes a fitting portion 221, which extends from the beveled annular surface 220 of the central passage toward the proximal fitting end 211. The central passage 213 then enlarges in diameter to form a fitting chamber 222. The fitting chamber 222 extends from a junction with the fitting portion 221 to a proximal tip 223 of the proximal fitting end 211.

An internally threaded region 224 of the fitting portion 221 of the central passage 213 extends from the junction of the fitting portion 221 and the fitting chamber 222 and extends toward the tapered distal tip 214 part way along the length of the fitting portion 221 and terminates just before the beveled annular surface 220.

The first ferrule 230 is slidably received within the central passage 213 of the tubular body 210 and, following assembly, engages the beveled annular surface 220 within the central passage 213 of the tubular body 210. The first ferrule 230 has frustoconical body 231 that defines a tapered outer surface 232. A central channel 233 extends through the frustoconical body 231. The first ferrule 230 can be molded, machined or otherwise formed from a suitable material such as thermoplastic resin, or a metal. In some implementations, the first ferrule 230 is formed from PEEK™.

The first compression screw 240 is inserted into the central passage 213 through the proximal tip 223, and is threaded into position, along the internally threaded region 224 within the central passage 213 of the tubular body 210, into contact with the first ferrule 230. When assembled, the first compression screw 240 forces the tapered outer surface 232 of the first ferrule 230 into contact with the beveled annular surface 220 within the central passage 213 of the tubular body 210. The first compression screw 240 has a cylindrical head 241 and an externally threaded cylindrical shaft 242. The externally threaded cylindrical shaft 242 and the internally threaded region 224 within the central passage 213 are provided with a mated thread, e.g., 10-32, ¼-28, 6 mm×1, etc. The externally threaded cylindrical shaft 242 is smaller in diameter that the cylindrical head 241 and is longer in length. A distal tip 243 of the externally threaded cylindrical shaft 242 defines a flat annular stop surface 244, which, following assembly, buts up against a proximal end 234 of the first ferrule 230. In some cases, the cylindrical head 241 can be provided with a knurled finish and/or one or more flattened surface regions which may help make it easier to grip the cylindrical head 241 when threading the compression screw 240 into the central passage 213.

An internal passage 245 extends the length of the first compression screw 240. The internal passage 245 has a small diameter region 246, which has a diameter that corresponds to that of the small diameter distal portion 219 within the central passage 213 of the tubular body 210 and the central channel 233 of the first ferrule 230, e.g., a diameter of 0.0355 inches to 0.0335 inches (e.g., 0.0345 inches). The small diameter region 246 extends from the distal tip 243 of the externally threaded cylindrical shaft 242 and flares outwardly at a tapered passage region 247 near a junction of the externally threaded cylindrical shaft 242 and the cylindrical head 241. The internal passage 245 also includes a cylindrical chamber 248 which extends from the tapered passage region 247 and terminates at a proximal tip 249 of the cylindrical head 241. The first compression screw 240 can have a single piece construction, being molded, machined or otherwise formed from a suitable material such as thermoplastic resin, or a metal. In some implementations, the first compression screw 241 is formed from polyimide (available as DUPONT VESPEL polyimide) or PEEK™.

During assembly, the first fluid tube 110 is fed through the internal passage 245 of the first compression screw 240, then through the central channel 233 of the first ferrule 230, and then though the central passage 213 of the tubular body 210 until a distal tip 111 (FIG. 2A) of the first fluid tube 110 sits flush with the opening of the central passage 213 at the center of the beveled annular recess 216. The first compression screw 240 can then be threaded into the central passage 213 forcing the tapered outer surface 232 of the first ferrule 230 into contact with the beveled annular surface 220 within the central passage of the tubular body 210 to fix the first fluid tube 110 in place relative to the tubular body 210. The first fluid tube 110 can have an inner diameter of 0.005 inches to 0.030 inches.

Figure 3A:
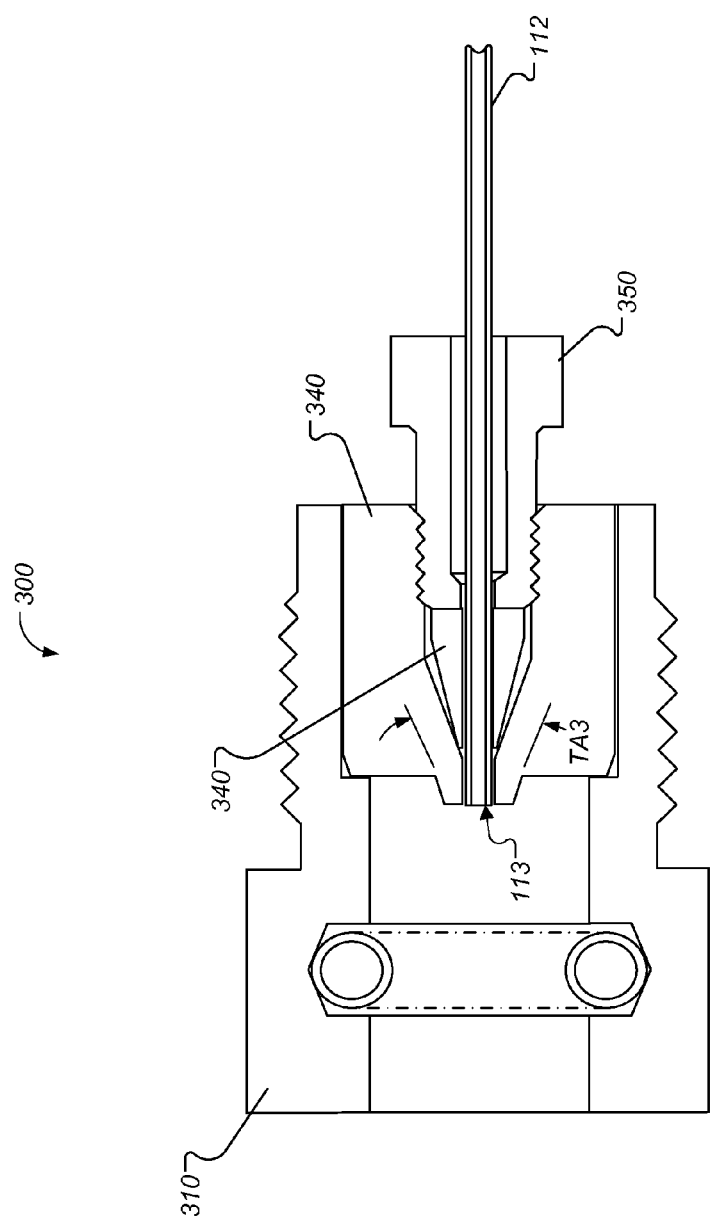
FIG. 3A is a cross-sectional view of the bulkhead fitting of FIG. 1B, taken along line 3A-3A.
Figure 3B:
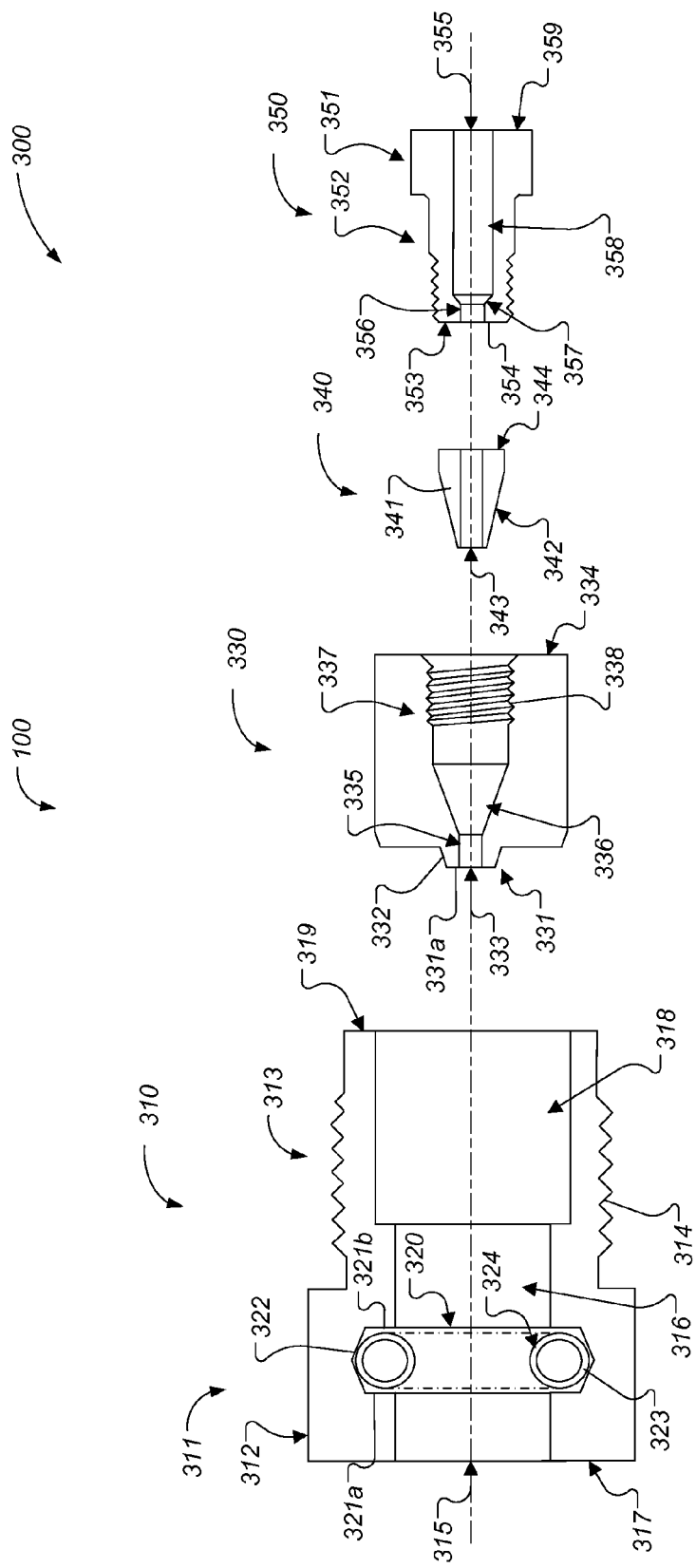
FIG. 3B is an exploded view of the bulkhead fitting of FIG. 3A.

Referring to FIGS. 3A & 3B, the bulkhead fitting 300 includes a fitting body 310, a cylindrical insert 330, a second ferrule 340, and a second compression screw 350. As shown in FIG. 3B, the fitting body 310 includes a head portion 311 with a knurled outer surface 312, and a stem portion 313 with an exterior threaded region 314. The exterior threaded region 314 can allow the bulkhead fitting 300 to be threaded into a fixed structure, such as a chassis. A cylindrical bore 315 includes a latching portion 316 which extends from a proximal tip 317 of the head portion 311 to a junction with the stem portion 313. The cylindrical bore 315 then enlarges in diameter to form an insert portion 318. The insert portion 318 extends from the juncture with the head portion 311 to a distal tip 319 of the stem portion 313 of the bulkhead fitting 300.

The bulkhead fitting 300 also includes a circumferential groove 320 within the latching portion 316 of the cylindrical bore 315. The latching portion 316 has a diameter of 0.236 inches to 0.240 inches (e.g., 0.238 inches), and the circumferential groove 320 has a diameter of 0.373 inches to 0.378 inches (e.g., 0.375 inches). The circumferential groove 320 has generally parallel sidewalls 321a, 321b and a tapered, v-shaped bottom 322. The circumferential groove 320 receives and retains a garter spring 323. The garter spring 323 has an outside diameter that is slightly larger than the diameter of the circumferential groove 320 so that upon inserting the garter spring 323 into the circumferential groove 320 it creates interference with the outside diameter of the garter spring 323 and the diameter of the circumferential groove 320. The interference provides a radial compression load that retains the garter spring 323 within the fitting body 310. The garter spring 323 can have an outside diameter of 0.390 inches to 0.400 inches (e.g., 0.395 inches), an inside diameter of 0.230 inches to 0.240 inches (e.g., 0.237 inches), a wire diameter of 0.010 inches to 0.014 inches (e.g., 0.012 inches), a coil width of 0.080 inches to 0.084 inches (e.g., 0.082 inches), and can be formed from stainless steel.

When assembled within the circumferential groove 320 of the fitting body 310, the garter spring 323 has a protruding portion 324 which protrudes radially into the latching portion 316 of the cylindrical bore 315. In this regard, the garter spring 323 provides for a latching connection with the male fitting 200. That is, the annular groove 217 of the male fitting 200, when aligned with the circumferential groove 320 of the bulkhead fitting 300 with the garter spring 323 therebetween, provides a latching action to maintain a physical connection between the male fitting 200 and the bulkhead fitting 300. The fitting body 310 can have a single piece construction, being molded, machined or otherwise formed from a suitable material such as thermoplastic resin, or a metal. In some implementations, the fitting body 310 is formed from stainless steel.

The cylindrical insert 330 has an overall cylindrical configuration with a slight taper at a proximal end of the cylindrical insert 330 to facilitate insertion into the insert portion 318 within the cylindrical bore 315 of the fitting body 310. The taper terminates at a proximal surface 331. The proximal surface 331 defines a frustoconical protrusion 332 which terminates at a proximal sealing face 331a. The frustoconical protrusion 332 is sized to fit within the beveled annular recess 216 of the male fitting 200, such that the proximal sealing face 331 abuts against the distal sealing face 215a of the male fitting 200 to form a fluid tight seal, e.g., up to 2500 pounds per square inch (PSI), when the male fitting 200 and the bulkhead fitting 300 are connected. The frustoconical protrusion 332 has a diameter of 0.059 inches to 0.065 inches (e.g., 0.062 inches) at its tip (i.e., at a junction with the proximal sealing face 331a), a height of 0.027 inches to 0.037 inches (e.g., 0.032 inches), and a taper angle TA3 of 29.5 degrees to 30.5 degrees (e.g., 30.0 degrees).

The cylindrical insert 330 has a central passage 333 that extends from the frustoconical protrusion 332 to a distal end 334 of the cylindrical insert 330. The central passage 333 has small diameter proximal portion 335 that flares outwardly to form a beveled annular surface 336. The beveled annular surface 336 thus defines a frustoconical recess formed centrally within the cylindrical insert 330. The central passage 333 also includes a fitting portion 337, which extends from the beveled annular surface 336 of the central passage 333 to the distal end 334.

The cylindrical insert 330 can have a single piece construction, being molded, machined or otherwise formed from a suitable material such as thermoplastic resin, or a metal. In some implementations, the cylindrical insert 330 is formed from stainless steel, and is finished along the proximal surface 331, at least at the proximal sealing face 331a, to have a surface roughness Ra of 4 microinches to 16 microinches (e.g., 8 microinches). Since the distal and proximal sealing faces 115a, 331a are substantially flat, a substantially zero dead volume fluidic connection is provided when the male and bulkhead fittings 200, 300 are connected.

During assembly, the cylindrical insert 330 is inserted into the insert portion 318 within the cylindrical bore 315 of the fitting body 310. In some cases, the cylindrical insert 330 is welded to the fitting body 310 following insertion. Alternatively or additionally, the cylindrical insert 330 may have an external diameter that is slightly larger than an internal diameter of the insert portion 318 of the cylindrical bore 315 and an interference fit is provided when the cylindrical insert 330 is inserted in the fitting body 310.

The second ferrule 340 is slidably received within the central passage of the cylindrical insert 330 and, following assembly, engages the beveled annular surface within the central passage 333 of the cylindrical insert 330. The second ferrule 340 has frustoconical body 341 that defines a tapered outer surface 342. A central channel 343 extends through the frustoconical body 341 of the second ferrule 340. The second ferrule 340 can be molded, machined or otherwise formed from a suitable material such as thermoplastic resin, or a metal. In some implementations, the second ferrule 340 is formed from PEEK™.

The second compression screw 350 is inserted into the central passage 333 of the cylindrical insert 330 through the distal end 334, and is threaded into position, along an internally threaded region 338 within the central passage 333 of the cylindrical insert 330, into contact with the second ferrule 340. When assembled, the second compression screw 350 forces the tapered outer surface 342 of the second ferrule 340 into contact with the beveled annular surface 336 within the central passage 333 of the cylindrical insert 330. The second compression screw 350 has a cylindrical head 351 and an externally threaded cylindrical shaft 352. The externally threaded cylindrical shaft 352 and the internally threaded region 338 within the central passage 333 of the cylindrical insert 330 are provided with a mated thread, e.g., 10-32, ¼-28, 6 mm×1, etc. The externally threaded cylindrical shaft 352 is smaller in diameter that the cylindrical head 351 and is longer in length. A proximal tip 353 of the externally threaded cylindrical shaft 352 defines a flat annular stop surface 354, which, following assembly, buts up against a distal end 344 of the second ferrule 340. In some cases, the cylindrical head 351 can be provided with a knurled finish and/or one or more flattened surface regions which may help make it easier to grip the cylindrical head 351 when threading the compression screw 350 into the central passage 333.

An internal passage 355 extends the length of the second compression screw 350. The internal passage 355 has a small diameter region 356, which has a diameter that corresponds to that of the small diameter proximal portion 335 within the central passage 333 of the cylindrical insert 330 and the central channel 343 of the second ferrule 340, e.g., a diameter of 0.0355 inches to 0.0335 inches (e.g., 0.0345 inches). The small diameter region 356 extends from the proximal tip 353 of the externally threaded cylindrical shaft 352 and flares outwardly at a tapered passage region 357 near a junction of the externally threaded cylindrical shaft 352 and the cylindrical head 351. The internal passage 355 also includes a cylindrical chamber 358 which extends from the tapered passage region 357 and terminates at a distal tip 359 of the cylindrical head 351. The second compression screw 350 can have a single piece construction, being molded, machined or otherwise formed from a suitable material such as thermoplastic resin, or a metal. In some implementations, the second compression screw 350 is formed from polyimide (available as DUPONT VESPEL polyimide) or PEEK™.

During assembly, the cylindrical insert 330 is slid into the insert portion 318 of the cylindrical bore 315 of the fitting body 310 and is fixed in place (e.g., via welds). A second fluid tube 112 is then fed through the internal passage 355 of the second compression screw 350, then through the central channel of the second ferrule 340, and finally though the central passage 333 of the cylindrical insert 330 until a proximal tip 113 (FIG. 3A) of the second fluid tube 112 sits flush with the opening of the central passage 333 at the center of the frustoconical protrusion 332. The second compression screw 350 can then be threaded into the central passage 333 of the cylindrical insert 330 forcing the tapered outer surface 342 of the second ferrule 340 into contact with the beveled annular surface 336 within the central passage 333 of the cylindrical insert 330 to fix the second fluid tube 112 in place relative to the fitting body 310. The second fluid tube 112 can have an inner diameter of 0.005 inches to 0.030 inches.

Figure 4:
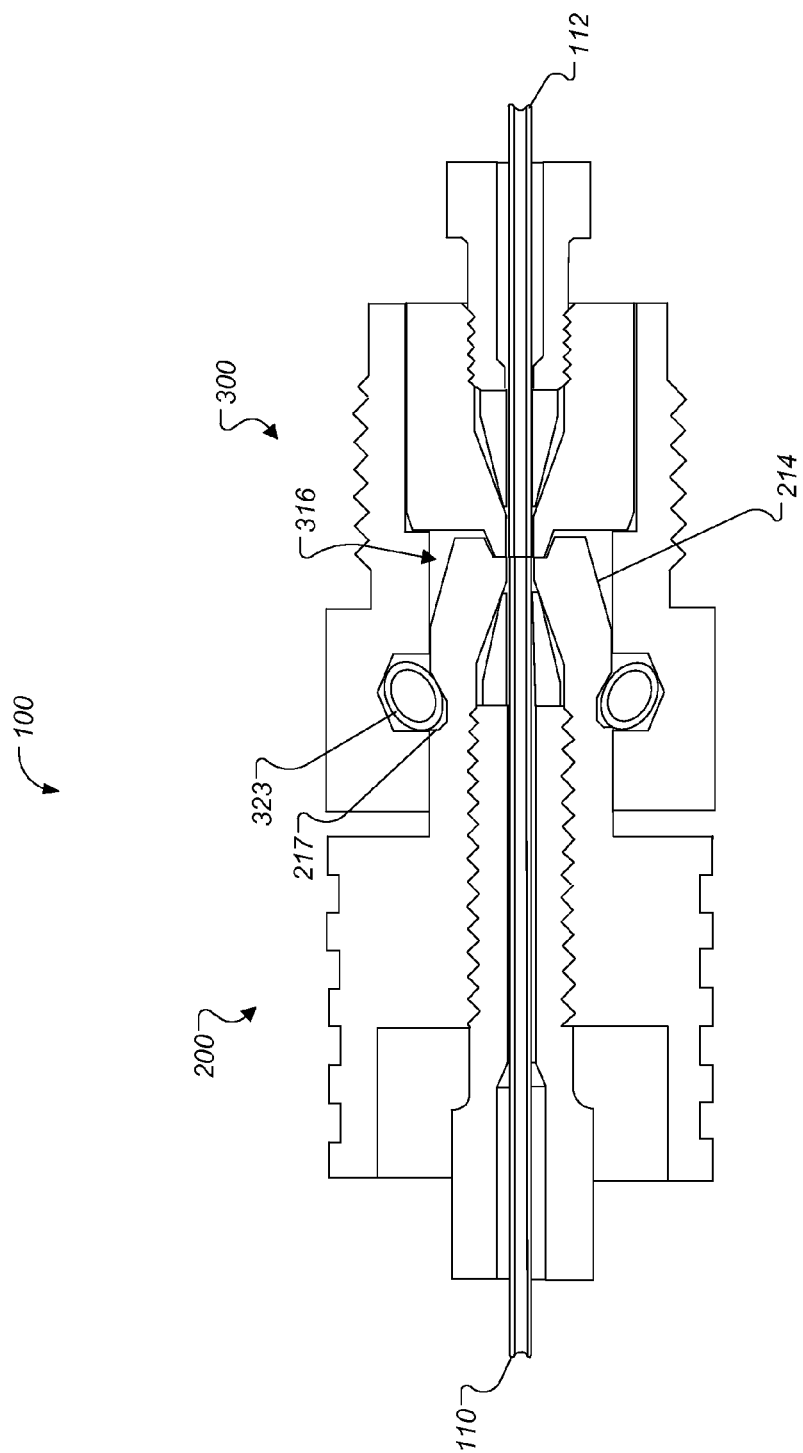
FIG. 4 is a cross-sectional side view of the quick connect fitting assembly of FIG. 1A, taken along line 4-4.

Once the male fitting 200 and the bulkhead fitting 300 are separately assembled with the first and second fluid tubes 110, 112, respectively, the male fitting 200 and the bulkhead fitting 300 can be connected to provide for fluid communication between the first and second fluid tubes 110, 112. The connection is achieved by inserting the tapered distal tip 214 of the male fitting 200 into the latching portion 316 of the cylindrical bore 315 of the bulkhead fitting 300 until the garter spring 323, residing within the bulkhead fitting 300, engages the tapered latching edge 217a of the annular groove 217, as illustrated in FIG. 4, thereby forming a latched connection. In some cases, a tactile and/or audible feedback (e.g., a tactile or audible snap) is provided when the garter spring 323 engages the annular groove 217.

Figure 5:
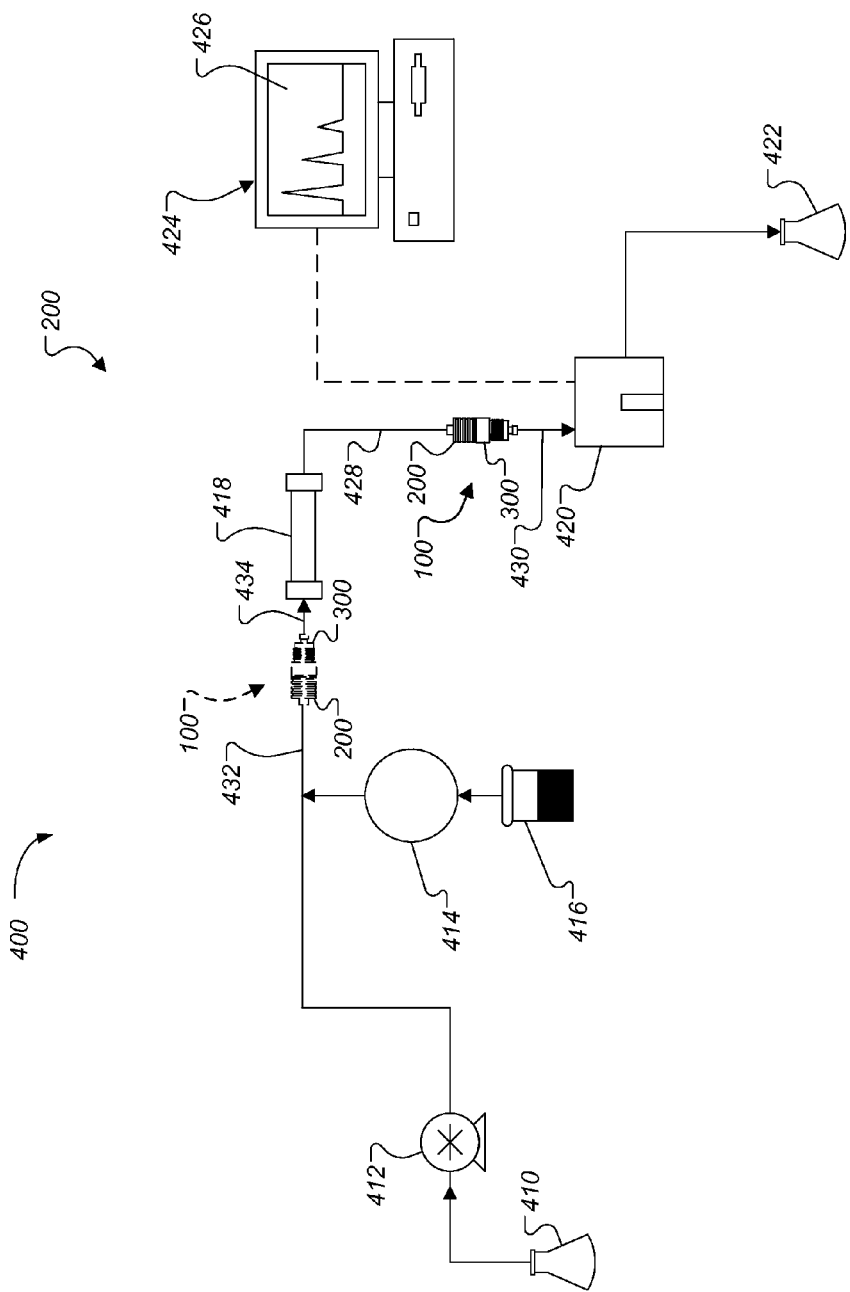
FIG. 5 is a schematic view of a chromatography system including the quick connect fitting assembly of FIG. 1A.

Once the male fitting 200 and the bulkhead fitting 300 are latched together, the proximal sealing face 331a at the proximal surface 331 of the bulkhead fitting 300 abuts against the distal sealing face 215a at the distal surface 215 of the male fitting 200 thereby forming a fluid tight seal with substantially no dead volume. Alternatively or additionally, the frustoconical protrusion 332 can be sized to have an interference fit with the beveled annular recess 216, such that the tapered walls of the frustoconical protrusion 332 engage the tapered walls of the beveled annular recess 216 to provide a fluid tight seal. A quick connect fitting assembly with this configuration can be used for making fluidic connections in chromatography systems. For example, FIG. 5 illustrates a liquid chromatography (LC) system 400 that incorporates the quick connect fitting assembly 100 of FIG. 1A. Referring to FIG. 5, a carrier fluid reservoir 410 holds a carrier fluid. A carrier fluid pump 412 is used to generate and meter a specified flow rate of the carrier fluid, typically milliliters per minute. The carrier fluid pump 412 delivers the carrier fluid to an injector 414. The injector 414 accurately and precisely introduces a discrete, predetermined volume of a sample solution, from a sample source 416 (e.g., a sample vial), into the flow of carrier fluid where it can combine with the flow of carrier fluid, which then carries the discrete, predetermined volume of the sample solution into a chromatography column 418. The injector 414 can be a simple manual device, or a sophisticated autosampler. A detector 420 is employed to detect separated compound bands as they elute from the chromatography column 418. The detector 420 can include a UV detector, an evaporative-light-scattering detector (ELSD), a mass spectrometer, and combination thereof. In some examples, the detector 420 can include a downstream microfluidic liquid chromatography-mass spectroscopy (LC-MS) system, such as the Trizaic™ UPLC® System with nanoTile™ technology, available from Waters Corporation of Milford, Mass. The carrier fluid exits the detector 420 and can be sent to waste 422 or collected, as desired. The detector 420 is wired to a computer data station 424, which records an electrical signal that is used to generate a chromatogram on its display 426.

As shown in FIG. 5, the quick connect fitting assembly 100 can be used to provide a fluidic connection between an output of the chromatography column 418 and an input of the detector 420. In this regard, the male fitting 200 can be attached to a fluid line 428 off the chromatography column 418 and the bulkhead fitting 300 can be attached to another fluid line 430 leading into the detector 420. In some cases, the bulkhead fitting 300 is fixedly mounted to a chassis.

Alternatively or additionally, the quick connect fitting assembly 100 can be used to provide a fluidic connection between an output of the injector 420 and an input of the chromatography column 418. In this case, the male fitting 200 can be attached to a fluid line 432 off the injector 420 and the bulkhead fitting 300 can be attached to another fluid line 434 leading into the chromatography column 418.

A number of implementations have been described. Nevertheless, it will be understood that various modifications may be made without departing from the spirit and scope of the invention.

What is claimed is:

1. A fitting assembly comprising:
   a first fitting configured to receive a first fluid tube, the first fitting defining a first groove and having a distal end that terminates at a distal-facing surface that defines a first sealing face;
   a second fitting configured to receive a second fluid tube, the second fitting comprising:
      a proximal-facing surface that defines a second sealing face; and
      a spring configured to engage the first groove to connect the first and second fittings such that the first and second fluid tubes are placed in fluid communication and a fluid tight seal is established between the first and second fittings where the first sealing face abuts the second sealing face.

2. The fitting assembly of claim 1, wherein the first sealing face of the first fitting defines a recess, and the second sealing face of the second fitting defines a protrusion, and wherein the protrusion is sized to fit within the recess such that the first sealing face abuts against the second sealing face to form the fluid tight seal when the first and second fittings are connected.

3. The fitting assembly of claim 1, wherein the first sealing face of the first fitting defines a recess, and the second sealing face of the second fitting defines a protrusion, and wherein the recess and the protrusion have an interference fit to form the fluid tight seal when the first and second fittings are connected.

4. The fitting assembly of claim 1, wherein the second fitting comprises a fitting body defining a cylindrical bore, and wherein the first fitting comprises a tubular body configured to be at least partially inserted into the cylindrical bore to establish a connection between the first and second fittings.

5. The fitting assembly of claim 4, wherein the spring is disposed within the cylindrical bore.

6. The fitting assembly of claim 4, wherein the fitting body defines a second groove within the cylindrical bore, and wherein the spring is disposed within the second groove.

7. The fitting assembly of claim 1, wherein the spring is a garter spring.

8. The fitting assembly of claim 1, wherein the fluid tight seal is fluid tight at least up to 2500 pounds per square inch (PSI).

9. The fitting assembly of claim 1, wherein the first fitting comprises a tubular body defining a central passage for receiving the first fluid tube.

10. The fitting assembly of claim 9, wherein the tubular body includes a beveled annular surface within the central passage, and
    wherein the first fitting comprises a ferrule configured to engage the beveled annular surface and to receive and retain the first fluid tube.

11. The fitting assembly of claim 10, wherein the tubular body includes an internally threaded region within the central passage, and
    wherein the first fitting comprises a compression screw configured to threadingly engage the internally threaded region to retain the ferrule within the central passage.

12. The fitting assembly of claim 11, wherein the compression screw comprises an internal passage configured to receive the first fluid tube.

13. The fitting assembly of claim 9, wherein the tubular body comprises a first fitting end having knurled outer surface, and a second fitting end defining a tapered tip, and wherein the second fitting end defines the first groove.

14. The fitting assembly of claim 9, wherein the first groove extends annularly about the tubular body.

15. The fitting assembly of claim 1, wherein the second fitting comprises:
    an insert defining a central passage for receiving the second fluid tube; and
    a fitting body defining a bore configured to receive the insert.

16. The fitting assembly of claim 15, wherein the bore includes a latching portion for receiving the first fitting, and an insert portion for receiving the insert.

17. The fitting assembly of claim 16, wherein the fitting body defines a second groove within the latching portion of the bore, and wherein the spring is disposed within the second groove.

18. The fitting assembly of claim 15, wherein the insert includes a beveled annular surface within the central passage, and
    wherein the second fitting comprises a ferrule configured to engage the beveled annular surface and to receive and retain the second fluid tube.

19. The fitting assembly of claim 18, wherein the insert includes an internally threaded region within the central passage, and
    wherein the second fitting comprises a compression screw configured to threadingly engage the internally threaded region to retain the ferrule within the central passage.

20. The fitting assembly of claim 19, wherein the compression screw comprises an internal passage configured to receive the second fluid tube.

21. A chromatography system comprising the fitting assembly of claim 1.

22. The chromatography system of claim 21, comprising:
a chromatography column; and
a detector for measuring physical or chemical properties of fluid received from the chromatography column,
wherein the fitting assembly is disposed between the chromatography column and the detector for establishing a fluidic connection therebetween.

23. The chromatography system of claim 21, comprising
a chromatography column; and
a pump for conveying fluid toward the chromatography column,
wherein the fitting assembly is disposed between the chromatography column and the pump for establishing a fluidic connection therebetween.

24. The fitting assembly of claim 2, wherein the protrusion has a frustoconical shape and is sized to fit within a beveled annular shape of the recess.

* * * * *